(12) United States Patent
Fox et al.

(10) Patent No.: US 7,396,542 B2
(45) Date of Patent: *Jul. 8, 2008

(54) STABLE PHARMACEUTICAL FORMULATION OF PAROXETINE HYDROCHLORIDE ANHYDROUS AND A PROCESS FOR PREPARATION THEREOF

(75) Inventors: Michael Fox, Tel Aviv (IL); Rakefet Cohen, Zur Yigal (IL); Anne Braunstein, Modiin (IL); Minutza Leibovici, Netanya (IL)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 0 days.

This patent is subject to a terminal disclaimer.

(21) Appl. No.: 10/330,969

(22) Filed: Dec. 27, 2002

(65) Prior Publication Data

US 2003/0144324 A1    Jul. 31, 2003

Related U.S. Application Data

(60) Provisional application No. 60/344,120, filed on Dec. 28, 2001, provisional application No. 60/366,351, filed on Mar. 21, 2002.

(51) Int. Cl.
*A61K 9/20* (2006.01)
*A61K 9/14* (2006.01)

(52) U.S. Cl. .......... 424/464; 424/465; 424/489
(58) Field of Classification Search .............. 424/400, 424/451, 464, 466, 474, 489, 465
See application file for complete search history.

(56) References Cited

U.S. PATENT DOCUMENTS

| | | | |
|---|---|---|---|
| 4,007,196 A | 2/1977 | Christensen et al. |
| 4,721,723 A | 1/1988 | Barnes et al. |
| 5,776,969 A | 7/1998 | James |
| 5,872,132 A * | 2/1999 | Ward et al. |
| 6,066,643 A | 5/2000 | Perry |
| 6,113,944 A | 9/2000 | Pathak et al. |
| 6,150,376 A | 11/2000 | Kozikowski et al. |
| 6,168,805 B1 | 1/2001 | Hein, II et al. |
| 6,228,864 B1 | 5/2001 | Smith et al. |
| 6,645,523 B2 * | 11/2003 | Lemmens et al. |
| 2001/0008896 A1 | 7/2001 | Smith et al. |
| 2002/0035145 A1 | 3/2002 | Tsai et al. |

(Continued)

FOREIGN PATENT DOCUMENTS

WO    WO 99/00313    1/1999

(Continued)

OTHER PUBLICATIONS

M. Ritala et al. "A Comparison Between Binders In The Wet Phase Of Ganulation In A High Shear Mixer" Drug Development and Industrial Pharmacy, vol. 12, No. 11-13, (1986), pp. 1685-1700, XP009058469.

(Continued)

*Primary Examiner*—Humera N Sheikh
(74) *Attorney, Agent, or Firm*—Kenyon & Kenyon LLP

(57) ABSTRACT

Provided are formulations of a stable commercial paroxetine tablet comprising paroxetine hydrochloride anhydrous, povidone, copovidone or HPMC as a binder, and an HCl free/non-hygroscopic filler, prepared by the wet granulation method.

18 Claims, 1 Drawing Sheet

U.S. PATENT DOCUMENTS

| | | |
|---|---|---|
| 2002/0048600 A1 | 4/2002 | Bhatt et al. |
| 2002/0065301 A1 | 5/2002 | Lemmens et al. |
| 2002/0156066 A1 | 10/2002 | Chen et al. |

FOREIGN PATENT DOCUMENTS

| | | |
|---|---|---|
| WO | WO 99/16440 | 4/1999 |
| WO | WO 99/65491 | 12/1999 |
| WO | WO 00/32593 | 6/2000 |
| WO | WO 00/71098 | 11/2000 |
| WO | WO 02/09710 | 2/2002 |
| WO | WO 02/069888 | 9/2002 |
| WO | WO 02/069969 | 9/2002 |

OTHER PUBLICATIONS

E. Draganoiu et al. "Evaluation Of The New Polyvinylacetate/ Povidone Excipient for Matrix Sustained Release Dosage Forms" Pharm. Ind., vol. 63, No. 6, (2001), pp. 624-629, XP009048713.

D. Flick et al. "Kollidon VA64" BASF ExAct, No. 5, (2000), p. 6-7, XP002357819.

D.M. Patel "Povidone" Handbook of Pharmaceutical Excipients, (1986), pp. 234-239, XP002060825.

* cited by examiner

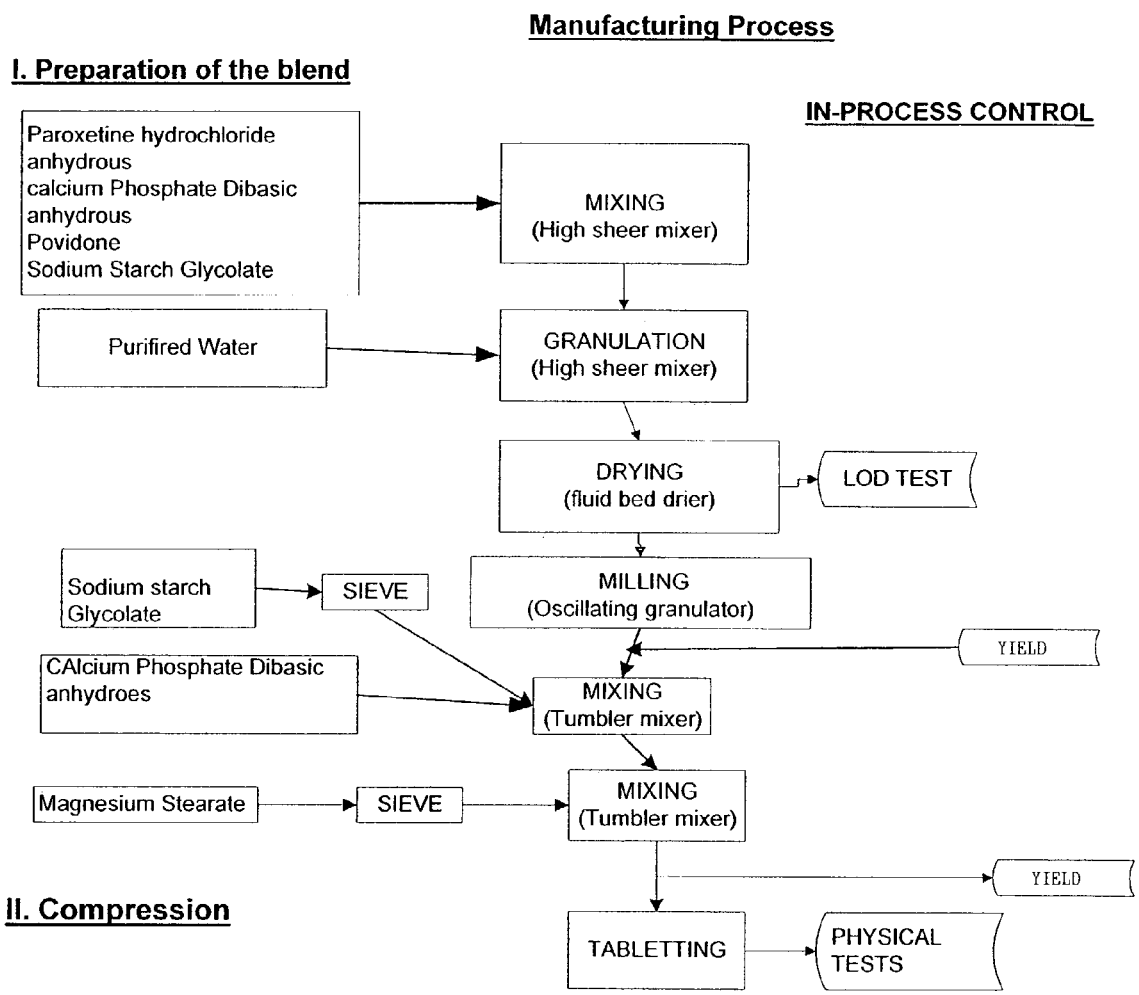
FIGURE 1- FLOW CHART OF THE MANUFACTURING PROCESS

STABLE PHARMACEUTICAL FORMULATION OF PAROXETINE HYDROCHLORIDE ANHYDROUS AND A PROCESS FOR PREPARATION THEREOF

CROSS-REFERENCE TO RELATED APPLICATIONS

This application claims the benefit of provisional application Ser. No. 60/344,120, filed Dec. 28, 2001 and provisional application Ser. No. 60/366,351, filed Mar. 21, 2002, both of which are incorporated herein by reference.

FIELD OF THE INVENTION

The present invention relates to pharmaceutical formulations of paroxetine hydrochloride anhydrous and their preparation.

BACKGROUND OF THE INVENTION

Paroxetine, trans (−)-3-[(1,3-benzodioxol-5-yloxy)methyl]-4-(4-fluorophenyl) piperidine, is a serotonin re-uptake inhibitor, and has the following molecular formula:

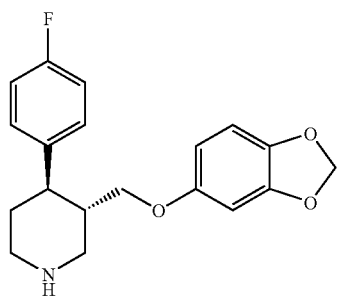

Paroxetine

Paroxetine, disclosed in U.S. Pat. No. 4,007,196 (incorporated herein by reference), is an orally administered antidepressant for the treatment of depression, social anxiety disorders, obsessive compulsive disorder, panic disorder, generalized anxiety disorder and posttraumatic stress disorder. Other syndromes such as pre-menstrual syndrome (PMS) and male sexual dysfunction can also be treated with paroxetine. Paroxetine is marketed as Paxil®, and in some countries as Seroxat® by GlaxoSmithKline.

Paxil® is prescribed as oral dosage tablets containing 10 mg, 20 mg, 30 mg and 40 mg of the base equivalent of paroxetine hydrochloride. Paxil® tablets include paroxetine hydrochloride hemihydrate, dibasic calcium phosphate dihydrate, hydroxypropyl methylcellulose, magnesium stearate, polyethylene glycols, polysorbate 80, sodium starch glycolate, titanium dioxide and one or more of the following: D&C Red No. 30, D&C Yellow No. 10, FD&C Blue No. 2, FD&C Yellow No. 6.

Paxil® is also available as an oral suspension with a dosage of 10 mg of the base equivalent of paroxetine hydrochloride in a 5 mL suspension containing paroxetine hydrochloride hemihydrate, polacrilin potassium, microcrystalline cellulose, propylene glycol, glycerin, sorbitol, methyl paraben, propyl paraben, sodium citrate dihydrate, citric acid anhydrous, sodium saccharin, flavorings, FD&C Yellow No. 6 and simethicone emulsion, USP.

Although Paxil® and Seroxat® contain HPMC, it is believed that HPMC is a component of the coating in these tablets, which are probably manufactured by a direct compression method. It is believed that these tablets do not contain a binder.

Paroxetine hydrochloride exists in two solid state pseudopolymorph forms differentiated by their degree of hydration. See e.g. U.S. Pat. No. 4,721,723, incorporated herein by reference. Form I is a non hygroscopic hemihydrate and is thermodynamically more stable. Form II is a hygroscopic anhydrate. Form II converts to Form I if seed crystals of Form I are present, when exposed to humid conditions, or if subject to compression.

Commercial paroxetine tablets, such as Paxil® and Seroxat® contain paroxetine as paroxetine hydrochloride (HCl) hemihydrate. According to U.S. Pat. No. 6,113,944, having the earliest priority date of Jun. 30, 1998, a tablet containing paroxetine hydrochloride anhydrous does not exist on the market.

A potential problem with paroxetine hydrochloride anhydrous tablets is the hygroscopic nature of the anhydrous form. U.S. Pat. No. 6,113,944 discloses formulating paroxetine hydrochloride anhydrous into tablets in the absence of water, i.e., dry admixing. WO 02/069969 discloses a certain formulation of paroxetine hydrochloride anhydrous prepared by wet granulation WO 02/069969 provides only one example, which uses microcrystalline cellulose as a filler and copovidone as a binder. WO 02/069969 also discloses that microcrystalline cellulose acts as the perfect excipient. According to WO 02/069969, "[I]t is surprising that in the present invention microcrystalline cellulose acts as a perfect [excipient]." However, microcrystalline cellulose may not be such a perfect excipient.

There is a need for new formulations of paroxetine hydrochloride anhydrous and processes for their preparation.

SUMMARY OF THE INVENTION

In one aspect, the present invention provides for an oral pharmaceutical dosage form comprising paroxetine hydrochloride anhydrous, a binder selected from the group consisting of povidone and copovidone, and a filler that is HCl free or non-hygroscopic, wherein the pharmaceutical dosage form is prepared by wet granulating paroxetine hydrochloride in the presence of a binder grade of povidone or copovidone, and the filler, to obtain an intra-granular portion of a granulate, and converting the granulate to the oral pharmaceutical dosage form.

In another aspect, the present invention provides for a process for preparing an oral pharmaceutical dosage form, comprising the steps of: wet granulating paroxetine hydrochloride anhydrous in the presence of a binder grade of a binder selected from the group consisting of povidone or copovidone, and an HCl free or a non-hygroscopic filler, to obtain an intra-granular portion of a granulate, drying the granulate, preparing a final blend from the granulate and converting the final blend to an oral pharmaceutical dosage form.

In another aspect, the present invention provides for a tablet comprising of the following active ingredient and excipients, in weight to weight percentages: about 10% to about 12.5% of paroxetine hydrochloride anhydrous, about 70% to about 90% of dibasic calcium phosphate anhydrous, about 1.5% to about 5% of sodium starch glycolate, about 0.5% to about 3% of magnesium stearate and about 2.5% to about 7.5% of povidone, wherein the tablet is prepared by wet granulating paroxetine hydrochloride anhydrous in the presence of povidone, dibasic calcium phosphate anhydrous and sodium starch glycolate to obtain a granulate, and converting the granulate to the tablet.

In another aspect, the present invention provides a process for preparing a paroxetine hydrochloride anhydrous tablet comprising the steps of: wet granulating with water as a processing solvent paroxetine hydrochloride anhydrous in the presence of sodium starch glycolate, Grade 29 to Grade 32 povidone and dibasic calcium phosphate anhydrous to obtain a granulate, drying the granulate to obtain LOD-NMT of about 1%; milling the granulate, mixing the granulate with an additional amount of sodium starch glycolate and calcium phosphate dibasic anhydrous, adding magnesium stearate to obtain a final blend and compressing the final blend to obtain the tablet.

In another aspect, the present invention provides for an oral pharmaceutical dosage form comprising paroxetine hydrochloride anhydrous, a binder grade of HPMC as a binder, and a filler that is HCl free or non-hygroscopic, wherein the pharmaceutical dosage form is prepared by wet granulating paroxetine hydrochloride in the presence of a binder grade of HPMC, and the filler, to obtain an intra-granular portion of a granulate, and converting the granulate to the oral pharmaceutical dosage form.

In another aspect, the present invention provides a process for preparing an oral pharmaceutical dosage form comprising the steps of: wet granulating paroxetine hydrochloride anhydrous in the presence of a binder grade of HPMC and an HCl free or a non-hygroscopic filler to obtain an intra-granular portion of a granulate, drying the granulate, preparing a final blend from the granulate and converting the final blend to an oral pharmaceutical dosage form.

In another aspect, the present invention provides a tablet comprising of the following active ingredient and excipients, in weight to weight percentages: about 10% to about 12.5% of paroxetine hydrochloride anhydrous as an active ingredient, about 70% to about 90% of dibasic calcium phosphate anhydrous, about 1.5% to about 5% of sodium starch glycolate, about 0.5% to about 3% of magnesium stearate and about 1% to about 4% of HPMC, wherein the tablet is prepared by wet granulating paroxetine hydrochloride anhydrous in the presence of HPMC, dibasic calcium phosphate anhydrous and sodium starch glycolate to obtain a granulate, and converting the granulate to the tablet.

In another aspect, the present invention provides for a process for preparing a paroxetine hydrochloride anhydrous tablet comprising the steps of: wet granulating with water as a processing solvent paroxetine hydrochloride anhydrous in the presence of sodium starch glycolate, HPMC with a viscosity of about 2 mPa*s to about 20 mPa*s for about a 2% solution in water at about 20° C. and dibasic calcium phosphate anhydrous to obtain a granulate, drying the granulate to obtain LOD-NMT of about 1%, milling the granulate, mixing the granulate with an additional amount of sodium starch glycolate and calcium phosphate dibasic anhydrous, adding magnesium stearate to obtain a final blend and compressing the final blend to obtain the tablet.

BRIEF DESCRIPTION OF THE FIGURES

FIG. 1 is a schematic diagram of a process for manufacturing paroxetine hydrochloride anhydrous tablets.

DETAILED DESCRIPTION OF THE INVENTION

The paroxetine hydrochloride tablets of the present invention are stable in that they remain substantially anhydrous during the manufacturing and coating process, i.e., free of water in the crystalline structure. Analysis such as DSC, PXRD, ICP or TGA can be performed to ascertain whether the paroxetine hydrochloride is anhydrous.

As used herein, the term "povidone" refers to a synthetic water-soluble homopolymer consisting of N-vinyl pyrrolidone. It has several chemical names including 1-ethenyl-2-pyrrolidinone polymers; 1-vinyl-2-pyrrolidinone polymers; poly[1-(2-oxo-1-pyrrolidinyl)ethylene]; polyvinlypyrrolidone; polyvidone; P.V.P.; RP 143, Kollidon; Peregal ST; Periston; Plasdone; Plasmosan; Protagent; Subtosan; Vinisil.

According to the *Handbook of Pharmaceutical Excipients*, published by the American pharmaceutical association, 3rd ed., povidone may be produced with an approximate molecular weight of from 2500 (grade K-12) to 3,000,000 (grade K-120). Povidone K-30 has an approximate molecular weight of 50,000.

Povidone Grade K 29-32 is a universal binder. Povidone Grade K-25 has an approximate molecular weight of about 30,000. Grade K-25 is similar to Grade K 29-32, but has lower viscosity which may be advantageous in some situations. Higher grades of povidone such as K-60 or K-90, with approximate molecular weights of 400,000 and 1,000,000 respectively, are used when higher binding capacity than the K 29-32 grade is needed.

The illustrations of the present invention use a K-30 Grade povidone because it is a universal binder. One of skill in the art would appreciate that other binder grades of povidone can be used. Preferably, the povidone used is Grade K29 to Grade K90, more preferably Grade K29 to Grade K32, and most preferably Grade K30.

Preferably, the amount of povidone to paroxetine hydrochloride used is about 20% to about 60% wt/wt ratio, i.e., weight of povidone compared to weight of paroxetine hydrochloride hemihydrate. More preferably, the ratio is about 30% to about 40%, and most preferably about 35% to about 40% wt/wt ratio.

It is believed that copovidone may be used in a similar fashion in the formulations of the present invention as povidone, in approximately the same amount and viscosity disclosed herein for povidone.

As used herein, the term hydroxypropyl methylcellulose ("HPMC") refers to a partly O-methylated and O-(2-hydroxypropylated) cellulose. It is also referred to as Benecel MHPC; hydroxypropyl methyl ether cellulose; E464; HPMC; Methocel; methylcellulose propylene glycol ether; methyl hydroxypropylcellulose; Metolose and Pharmacoat. Like povidone, hydroxypropyl methylcellulose comes in various grades having different vicosity. The present invention uses a binder grade HPMC in the wet granulation process. The viscosity of HPMC used is preferably from about 2 mPa*s to about 20 mPa*s for a 2% solution in water at about 20° C.

The ratio of HPMC to paroxetine hydrochloride is preferably from about 10% to about 30%, more preferably about 10% to about 25%, and most preferably from about 15% to about 25% weight to weight of HPMC to paroxetine hydrochloride.

The present invention provides for a paroxetine hydrochloride anhydrous tablets with povidone or HPMC as a binder, with a formulation that uses an HCl free/non-hygroscopic filler. Povidone and HPMC are used as intra-granular tablet core excipients. A tablet core excipient is an excipient used to make the core, as supposed to an excipient used in the coating process to coat the core. The tablet core is further divided to an intra-granular and extra-granular portion. Intra-granular excepients refers to excipients added during the granulation process, while extra-granular excipients refer to excipients added after the granulation process, but before compression, or other necessary steps to convert the final blend to a desired pharmaceutical dosage form.

The ratio of povidone and HPMC can also be expressed in relation to the intra-granular portion. Preferably, the amount of povidone to the intra-granular portion is about 2% to about 9% weight of povidone to weight of intra-granular portion which also includes weight of povidone. A more preferred range is about 3% to about 7%. The most preferred dose range is about 4% to about 7% weight to weight ratio. Preferably, the amount of HPMC to the intra-granular portion is about 1% to about 7%, more preferably about 2% to about 7%, and most preferably about 2% to about 6%, the weight of the intra-granular portion including the weight of HPMC.

For optimal result, the formulations of the present invention contain an HCl free filler or a non-hygroscopic filler, more preferably a filler having both characteristics. As used herein, "HCl free filler" refers to a filler that does not naturally contain and is not processed with HCl. Examples of such fillers include the sugars (e.g. lactose and mannitol, with mannitol being preferred), and more preferably dibasic calcium phosphate anhydrous. An example of an excipient that includes HCl is microcrystalline cellulose, which is prepared by depolymerization of natural cellulose. The depolymerization is believed to be catalyzed by use of HCl, which results in the presence of excess HCl, and a deterioration in the final product. Microrocrystalline cellulose is also hygroscopic, i.e., it absorbs water from its surrounding.

In addition to binders and fillers, the pharmaceutical compositions of the present invention can include other excipients known in the art, including both excepients for the tablet core and for the coating. For example, the dissolution rate of a compacted solid pharmaceutical composition in the patient's stomach may be increased by the addition of a disintegrant to the composition. Disintegrants include for example alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidone®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Suitable lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Glidants for example can be added to improve the flow properties of non-compacted solid composition and improve the accuracy of dosing. Excipients that may function as glidants include for example colloidal silicon dixoide, magnesium trisilicate, powdered cellulose, starch, talc and tribasic calcium phosphate.

Another class of excipients is flavoring agents and flavor enhancers make the dosage form more palatable to the patient. Common flavoring agents and flavor enhancers for pharmaceutical products include for example maltol, vanillin, ethyl vanillin, menthol, citric acid, fumaric acid, ethyl maltol, and tartaric acid. Various coloring agents can also be used.

In a preferred embodiment, other than having povidone or hydroxypropyl methylcellulose as a binder, and an HCl free filler such as dibasic calcium phosphate anhydrous, the pharmaceutical dosage form of the present invention also has a disintegrant such as sodium starch glycolate. The pharmaceutical dosage form of the present invention also preferably has a lubricant. Additionally, the tablet are preferably coated.

In one embodiment, the present invention provides a process for preparing an oral pharmaceutical dosage form, comprising the steps of wet granulating paroxetine hydrochloride anhydrous in the presence of a binder grade of a binder selected from the group consisting of povidone or copovidone, and an HCl free or a non-hygroscopic filler, to obtain an intra-granular portion of a granulate, drying the granulate, preparing a final blend from the granulate and converting the final blend to an oral pharmaceutical dosage form. In a preferred embodiment, the oral dosage form is a tablet, which is further coated.

Without being bound by any theory, it is believed that the presence of an effective amount of povidone and HPMC stabilizes the anhydrous form of paroxetine hydrochloride by preventing water molecules from incorporating into a paroxetine hydrochloride anhydrous crystal to yield a hemihydrate crystal. An HCl free/non-hygroscopic filler should be used with the povidone or HPMC for optimal result.

As illustrated by the flow chart of the manufacturing process and Table 1, the tablets may be prepared in a routine manner. Paroxetine hydrochloride anhydrous and povidone or HPMC are mixed together along with other excipients. Preferably, an effective amount of povidone or HPMC is used to keep the paroxetine hydrochloride in the granulate and/or the tablet substantially anhydrous, and avoid a transition to the hemihydrate form.

During the wet granulation, paroxetine hydrochloride anhydrous and povidone or HPMC are mixed with a disintegrant, such as sodium starch glycolate, and an HCl free filler (dibasic calcium phosphate anhydrous). The mixture is then wet granulated, preferably in a high sheer mixture in the presence of water as a processing solvent. The term wet granulation refers to granulation in the presence of an aqueous processing solvent, as supposed to granulation in the absence of any processing solvent or with a non-aqueous processing solvent. Preferably, the processing solvent of the wet granulation is water or a mixture of water and another water miscible solvent. Examples of such water miscible solvents include $C_1$ to $C_3$ alcohols and lower ketones. Preferred solvent mixtures include: water and acetone; water and methanol; water and ethanol; and water, methanol/ethanol and acetone. Use of water is most preferred. After wet granulation, the resulting granulate is then dried. Preferably the granulate is dried to LOD-NMT about 2%, more preferably to NMT about 1%.

In one embodiment the resulting intra-granular portion of the granulate is processed to prepare a final blend for compression. To process a granulate, the granulate is preferably milled and mixed with additional amounts of the disintegrant and filler. These excipients may be prepared for optimal results before mixing, such as by sieving. The excipients added after granulation can be of the same or different quality/grade of the same excipient used during the granulation process.

Preferably, a lubricant is added before compression to obtain a final blend. A lubricant known in the art, such as magnesium stearate, may be used. The resulting blend is then compressed into a tablet.

In one embodiment, the resulting tablets are coated, such as by Opadry® (Colorcon, Westpoint Pa.). According to Colorcon, Opadry® is a one-step customized coating system that combines polymer, plasticizer, and if desired, a pigment in dry concentrate. Preferably, the coating used for the tablets includes about 25% to about 35%, more preferably 30% titanium dioxide, about 25% to about 35%, more preferably about 30% hydroxypropyl methylcellulose, preferably about 5% to about 10%, more preferably about 8% polyethylene glycol and preferably about less than 1% to about 3%, more preferably about 1 percent polysorbate, respective weight to weight. The tablets can be coated by being warmed and then sprayed with a coating.

A preferred tablet of the present invention has the following weight to weight percentages: about 10% to about 12.5% of paroxetine hydrochloride anhydrous, about 70% to about 90% of dibasic calcium phosphate; about 1.5% to about 5% of sodium starch glycolate, about 0.5% to about 3% of magnesium stearate, about 2.5% to about 7.5% povidone or about 1% to about 4% of HPMC. The tablet preferably contains from about 3 mg to 12 mg of Opadry.®

As one skilled in the art would appreciate, the present invention is not limited to tablets and processes for their preparation. Tablets are a preferred dosage for paroxetine hydrochloride as evident in the manner Paxil® is marketed. The oral pharmaceutical dosage forms of the present invention, in addition to tablets, may be in the form of tablets, capsules, sachets, granules, suspension, effervescent tablets, chewable tablets and geltabs.

Optimal unit dosages of paroxetine hydrochloride anhydrous can be made for effective inhibition of serotonin re-uptake. The unit dosages of parxetine hydrochloride are preferably no more than about 100 mg, more preferably no more than about 50 mg, and most preferably about 10 mg, 20 mg, 30 mg and 40 mg of the base equivalent of paroxetine hydrochloride. The following non-limiting examples further illustrate the embodiments of the invention:

EXAMPLE

Example 1

Composition of Stable Tablets of Paroxetine Hydrochloride

A paroxetine hydrochloride tablet was made which was of anhydrous form despite use of wet granulation. A tablet composition of paroxetine hydrochloride anhydrous, as made, is provided in Table 1. The manufacturing process is provided after the table.

TABLE 1

Tablet Composition of Paroxetine Hydrochloride Anhydrous
[Includes extra-granular excipients]

| INGREDIENTS | Mg per tablet | FUNCTION |
|---|---|---|
| Cores | | |
| Paroxetine Hydrochloride Anhydrous | 22.21 | Active Ingredient |
| Povidone K-30 | 8 | binder |
| Dibasic Calcium Phosphate Anhydrous | 160.79 | Filler |
| Sodium starch Glycolate | 6.0 | Disintegrant |
| Magnesium Stearate | 3.0 | Lubricant |
| Purified water | Q.S. | Processing solvent (wet granulation) |

TABLE 1-continued

Tablet Composition of Paroxetine Hydrochloride Anhydrous
[Includes extra-granular excipients]

| INGREDIENTS | Mg per tablet | FUNCTION |
|---|---|---|
| Coating Suspension: | | |
| *Opadry ® | 6.0 | |
| *Composition of the Opadry ® | % W/W | |
| Titanium Dioxide | 31.250 | |
| Hydroxypropylmethylcellulose (Methocel E3 Premium) | 29.875 | |
| Hydroxypropylmethylcellulose (Methocel E5 Premium) | 29.875 | |
| Polyethylene Glycol 400 | 8.000 | |
| Polysorbate 80 (Tween) | 1.000 | |

Manufacturing Process of Stable Tablets of Paroxetine Hydrochloride Anhydrous

The manufacturing process of the cores was as follows:

A) Mixing of dibasic calcium phosphate anhydrous powder, paroxetine hydrochloride anhydrous, Povidone K-30 and sodium starch glycolate in a high sheer mixer (at room temperature=R.T.);

B) Addition of water to the high sheer mixer and mixing (at R.T.);

C) Drying of the granulate in a fluid bed drier: Inlet air temperature of about 60-70° C., and outlet air temperature to about 45° C.;

D) After the granulate was cooled down to R.T.: Checking LOD (NMT 1%). If LOD was higher than 1%, continue drying under the same conditions;

E) Milling of the dried granulate through a 0.6 sieve in the oscillating mill (R.T.);

F) Sieving of sodium starch glycolate trough a 30 mesh sieve (R.T.);

G) Mixing of the milled granulate from step E, sodium starch glycolate of step F and calcium phosphate dibasic anhydrous in a tumbler mixer (R.T.);

H) Sieving of magnesium stearate through a 50 mesh sieve;

I) Addition of magnesium stearate to the tumbler mixer from step G and further mixing; and J) Compression of tablets in the rotary machine (R.T.).

Coating:

A) Opadry® was mixed with purified water until a homogenous suspension was obtained;

B) The cores were placed in the coating machine and were warmed until outlet air temperature was 40 to 46° C. (Inlet air temp: 50-60° C.);

C) The coating suspension was sprayed through a nuzzle. Inlet air temperature was 60 to 70° C. and outlet temperature was 40-46° C. The cores preferably gain a weight of about 3%;

D) When the process was finished, the set point of the inlet air temperature was reduced to 25° C., spraying of the coating suspension was finished and the pan speed was reduced to minimum;

E) The coated tablets were taken out of the coating machine when the outlet air temperature was 30° C.

Example 2

Paroxetine Anhydrous Tablet with Hydroxypropyl Methylcellulose as a Binder (Prepared Generally by the Same Process Disclosed in Example 1):

Paroxetine HCl Anhydrous (app. 11% w/w).
Dibasic Calcium Phosphate Anhydrous (app. 82% w/w).

Hydroxypropyl Methylcellulose, Grade E-5 (app. 2% w/w).
Sodium Starch Glycolate (app. 3% w/w).
Magnesium Stearate (app. 1.5% w/w).
Purified Water (processing solvent only).

Example 3

Prophetic Example

The paroxetine hydrochloride tablet prepared in Example 1 is subjected to a mechanical test—(Kraemer® Tablets Test System)

| HARDNESS OF THE TABLETS, SCU INITIAL | HARDNESS OF THE TABLETS, SCU AFTER 24 HOURS, 80° C., 75% RELATIVE HUMIDITY |
|---|---|
| 16 | 16 |

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of excipients are disclosed for example in *Handbook of Pharmaceutical Excipients*, published by the American pharmaceutical association, 3rd ed. All references mentioned herein are incorporated in their entirety.

What is claimed is:

1. A tablet comprising of the following active ingredient and excipients, in weight to weight percentages:
   a) about 10% to about 12.5% of paroxetine hydrochloride anhydrous;
   b) about 70% to about 90% of dibasic calcium phosphate anhydrous;
   c) about 1.5% to about 5% of sodium starch glycolate;
   d) about 0.5% to about 3% of magnesium stearate; and
   e) about 2.5% to about 7.5% of one member selected from the group consisting of povidone and co-povidone,
wherein the tablet is prepared by wet granulating paroxetine hydrochloride anhydrous in the presence of povidone or copovidone, dibasic calcium phosphate anhydrous and sodium starch glycolate to obtain a granulate, and converting the granulate to the tablet, and with the proviso that the paroxetine hydrochloride remains substantially anhydrous during the wet granulation process.

2. The tablet of claim 1, further comprising about 3 to about 12 mg of a coating composition of about 30% titanium dioxide, about 30% hydroxypropyl methylcellulose, about 8% polyethylene glycol and about 1% polysorbate, respective weight to weight.

3. The tablet of claim 1, wherein the wet granulating is carried out with water as a processing solvent.

4. The tablet of claim 1, wherein the wet granulating is carried out with a mixture of water and a water miscible ketone or alcohol, or mixtures thereof as a processing solvent.

5. A method for inhibiting serotonin re-uptake comprising administering the tablet of claim 1 to a mammal.

6. A process for preparing a paroxetine hydrochloride anhydrous tablet according to claim 1 comprising the steps of:
   a) wet granulating with water as a processing solvent paroxetine hydrochloride anhydrous in the presence of sodium starch glycolate, Grade 29 to Grade 32 povidone and dibasic calcium phosphate anhydrous to obtain a granulate;
   b) drying the granulate to obtain LOD-NMT of about 1%;
   c) milling the granulate;
   d) mixing the granulate with an additional amount of sodium starch glycolate and calcium phosphate dibasic anhydrous;
   e) adding magnesium stearate to obtain a final blend; and
   f) compressing the final blend to obtain the tablet.

7. A tablet comprising the following active ingredient and excipients, in weight to weight percentages:
   a) about 10% to about 12.5% of paroxetine hydrochloride anhydrous as an active ingredient;
   b) about 70% to about 90% of dibasic calcium phosphate anhydrous;
   c) about 1.5% to about 5% of sodium starch glycolate;
   d) about 0.5% to about 3% of magnesium stearate; and
   e) about 1% to about 4% of HPMC,
wherein the tablet is prepared by wet granulating paroxetine hydrochloride anhydrous in the presence of HPMC, dibasic calcium phosphate anhydrous and sodium starch glycolate to obtain a granulate, and converting the granulate to the tablet, and with the proviso that the paroxetine hydrochloride remains substantially anhydrous during the wet granulation process.

8. The tablet of claim 7, further comprising about 3 to about 12 mg of a coating composition of about 30% titanium dioxide, about 30% hydroxypropyl methylcellulose, about 8% polyethylene glycol and about 1% polysorbate, respective weight to weight.

9. The tablet of claim 7, wherein the wet granulating is carried out with water as a processing solvent.

10. The tablet of claim 7, wherein the wet granulating is carried out with a mixture of water and a water miscible ketone or alcohol, or mixtures thereof as a processing solvent.

11. A method for inhibiting the re-uptake of serotonin comprising administering the tablet of claim 7 to a mammal.

12. A process for preparing a paroxetine hydrochloride anhydrous tablet according to claim 8 comprising the steps of:
   a) wet granulating with water as a processing solvent paroxetine hydrochloride anhydrous in the presence of sodium starch glycolate, HPMC with a viscosity of about 2 mPa*s to about 20 mPa*s for about a 2% solution in water at about 20° C. and dibasic calcium phosphate anhydrous to obtain a granulate;
   b) drying the granulate to obtain LOD-NMT of about 1%;
   c) milling the granulate;
   d) mixing the granulate with an additional amount of sodium starch glycolate and calcium phosphate dibasic anhydrous;
   e) adding magnesium stearate to obtain a final blend; and
   f) compressing the final blend to obtain the tablet.

13. The tablet of claim 1, wherein the tablet comprises povidone.

14. The tablet of claim 1, wherein the tablet comprises co-povidone.

15. A tablet comprising the following active ingredient and excipients, in weight to weight percentages:
   a) about 10% to about 12.5% of paroxetine hydrochloride anhydrous;

b) about 70% to about 90% of dibasic calcium phosphate anhydrous;
c) about 1.5% to about 5% of sodium starch glycolate;
d) about 0.5% to about 3% of magnesium stearate; and
e) about 2.5% to about 7.5% of one member selected from the group consisting of povidone and co-povidone.

16. The tablet of claim 15, wherein the tablet comprises povidone.

17. The tablet of claim 15, wherein the tablet comprises co-povidone.

18. A tablet comprising the following active ingredient and excipients, in weight to weight percentages:
a) about 10% to about 12.5% of paroxetine hydrochloride anhydrous as an active ingredient;
b) about 70% to about 90% of dibasic calcium phosphate anhydrous;
c) about 1.5% to about 5% of sodium starch glycolate;
d) about 0.5% to about 3% of magnesium stearate; and
e) about 1% to about 4% of HPMC.

* * * * *